(12) United States Patent
Watanabe et al.

(10) Patent No.: US 9,804,398 B2
(45) Date of Patent: Oct. 31, 2017

(54) HEAD-MOUNTED PERFUME DISPENSER APPARATUS

(71) Applicant: Panasonic Intellectual Property Corporation of America, Torrance, CA (US)

(72) Inventors: Yasuhito Watanabe, Osaka (JP); Taiji Sasaki, Osaka (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 229 days.

(21) Appl. No.: 14/708,264

(22) Filed: May 10, 2015

(65) Prior Publication Data

US 2015/0241708 A1   Aug. 27, 2015

Related U.S. Application Data

(63) Continuation of application No. PCT/JP2014/004221, filed on Aug. 19, 2014.

(30) Foreign Application Priority Data

Aug. 23, 2013   (JP) .................................. 2013-173295

(51) Int. Cl.
*H04N 5/765*   (2006.01)
*G02B 27/01*   (2006.01)
(Continued)

(52) U.S. Cl.
CPC ......... *G02B 27/0176* (2013.01); *A45D 34/02* (2013.01); *A61L 9/032* (2013.01);
(Continued)

(58) Field of Classification Search
CPC ........ A63J 20/008; A45D 34/02; A61L 9/032; A61L 9/035; G02B 2027/0178; G02B 27/0176; G11B 27/11
(Continued)

(56) References Cited

U.S. PATENT DOCUMENTS 1,749,187 A * 3/1930 Leavell .................. G03B 15/08
                                                        352/85
2,540,144 A * 2/1951 Stern ........................ H04N 7/08
                                                        340/12.17
(Continued)

FOREIGN PATENT DOCUMENTS

EP        2416305 A  *  1/2006
JP        61-041229 A  *  2/1986
(Continued)

OTHER PUBLICATIONS

International Search Report of PCT application No. PCT/JP2014/004221 dated Oct. 14, 2014.

*Primary Examiner* — David Harvey
(74) *Attorney, Agent, or Firm* — Greenblum & Bernstein, P.L.C.

(57) ABSTRACT

A head-mounted display includes a playback processor which plays back a moving image from first time until second time, a box for placing a container containing a perfume inside, a filled section which is temporarily filled with the perfume and emits the temporarily filled perfume according to starting playback of the moving image, and a tubular vent hole which is in contact with a nose of a user when the user wears the head-mounted display.

11 Claims, 15 Drawing Sheets

(51) Int. Cl.
*G09F 19/00* (2006.01)
*A45D 34/02* (2006.01)
*A61L 9/03* (2006.01)
*G11B 27/11* (2006.01)
*H04N 5/64* (2006.01)

(52) U.S. Cl.
CPC .............. *A61L 9/035* (2013.01); *G09F 19/00* (2013.01); *G11B 27/11* (2013.01); *G02B 2027/0178* (2013.01); *H04N 5/64* (2013.01)

(58) Field of Classification Search
USPC ........................................................ 386/200
See application file for complete search history.

(56) References Cited

U.S. PATENT DOCUMENTS

| | | | | |
|---|---|---|---|---|
| 2,905,049 | A * | 9/1959 | Laube | A61L 9/122 141/126 |
| 3,628,829 | A * | 12/1971 | Heilig | A47C 1/12 297/180.14 |
| 4,942,488 | A * | 7/1990 | Osawa | G11B 20/00086 348/E5.143 |
| 5,398,070 | A * | 3/1995 | Lee | H04N 5/44 261/107 |
| 5,591,409 | A * | 1/1997 | Watkins | A61L 9/035 422/1 |
| 5,610,674 | A * | 3/1997 | Martin | B01F 3/022 352/85 |
| 5,724,256 | A * | 3/1998 | Lee | A61L 9/125 422/105 |
| 5,734,590 | A * | 3/1998 | Tebbe | A61L 9/125 700/94 |
| 5,949,522 | A * | 9/1999 | Manne | A61L 9/122 261/104 |
| 6,025,902 | A * | 2/2000 | Wittek | A61L 9/04 297/217.3 |
| 6,149,873 | A * | 11/2000 | Potter | G06F 3/011 239/271 |
| 6,338,818 | B2 * | 1/2002 | Budman | A61L 9/035 261/107 |
| 7,154,579 | B2 * | 12/2006 | Selander | A61L 9/125 352/40 |
| 7,718,119 | B2 * | 5/2010 | Tajima | A61L 9/122 222/146.5 |
| 8,447,824 | B2 * | 5/2013 | Hong | H04N 21/23614 370/230 |
| 2002/0018181 | A1 * | 2/2002 | Manne | A61L 9/122 352/85 |
| 2003/0026728 | A1 * | 2/2003 | Avram | A63J 5/00 422/4 |
| 2003/0223040 | A1 * | 12/2003 | Schermerhorn | G03B 21/32 352/85 |
| 2005/0226601 | A1 * | 10/2005 | Cohen | H04N 7/165 386/263 |
| 2005/0244307 | A1 * | 11/2005 | Gygax | A61L 9/035 422/124 |
| 2006/0065986 | A1 * | 3/2006 | Morie | A61K 8/02 261/26 |
| 2008/0049960 | A1 * | 2/2008 | Petersen | H04R 1/083 381/375 |
| 2008/0289704 | A1 * | 11/2008 | Verstegen | A61L 9/03 137/560 |
| 2010/0309434 | A1 * | 12/2010 | Van Schijndel | A61L 9/125 352/85 |
| 2011/0250962 | A1 * | 10/2011 | Feiner | A63F 13/213 463/31 |
| 2012/0325941 | A1 | 12/2012 | Nakamoto et al. | |
| 2015/0019030 | A1 * | 1/2015 | Chandler | G05D 7/0629 700/283 |
| 2015/0048178 | A1 * | 2/2015 | Edwards | A61L 9/032 239/13 |
| 2016/0067367 | A1 * | 3/2016 | Jin | A61L 9/12 422/4 |

FOREIGN PATENT DOCUMENTS

| | | | |
|---|---|---|---|
| JP | 2001-036829 A | * | 2/2001 |
| JP | 2011-166430 A | * | 2/2010 |
| JP | 2011-184486 | | 9/2011 |
| JP | 2013-074476 | | 4/2013 |
| WO | 2013/005615 | | 1/2013 |

* cited by examiner

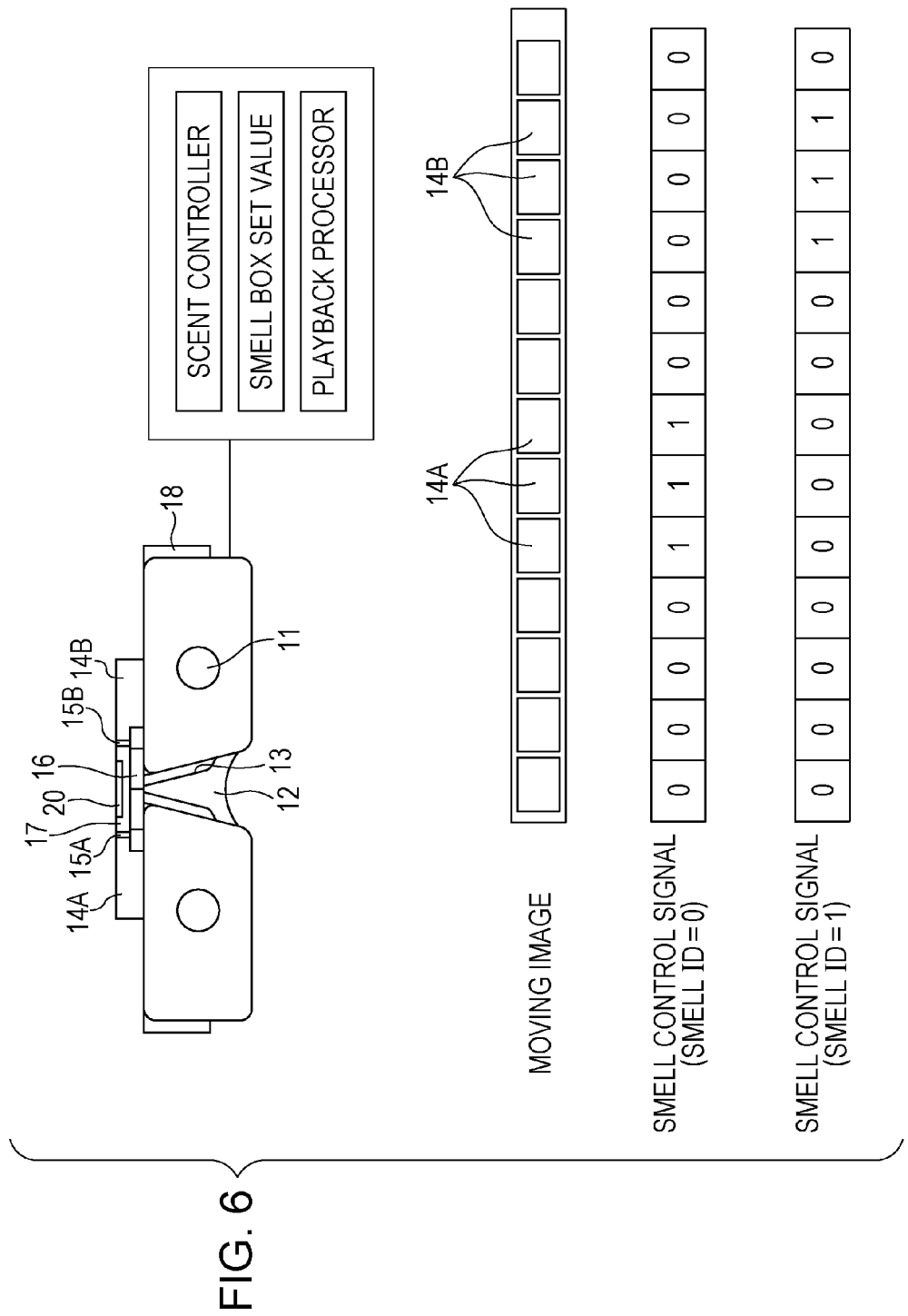

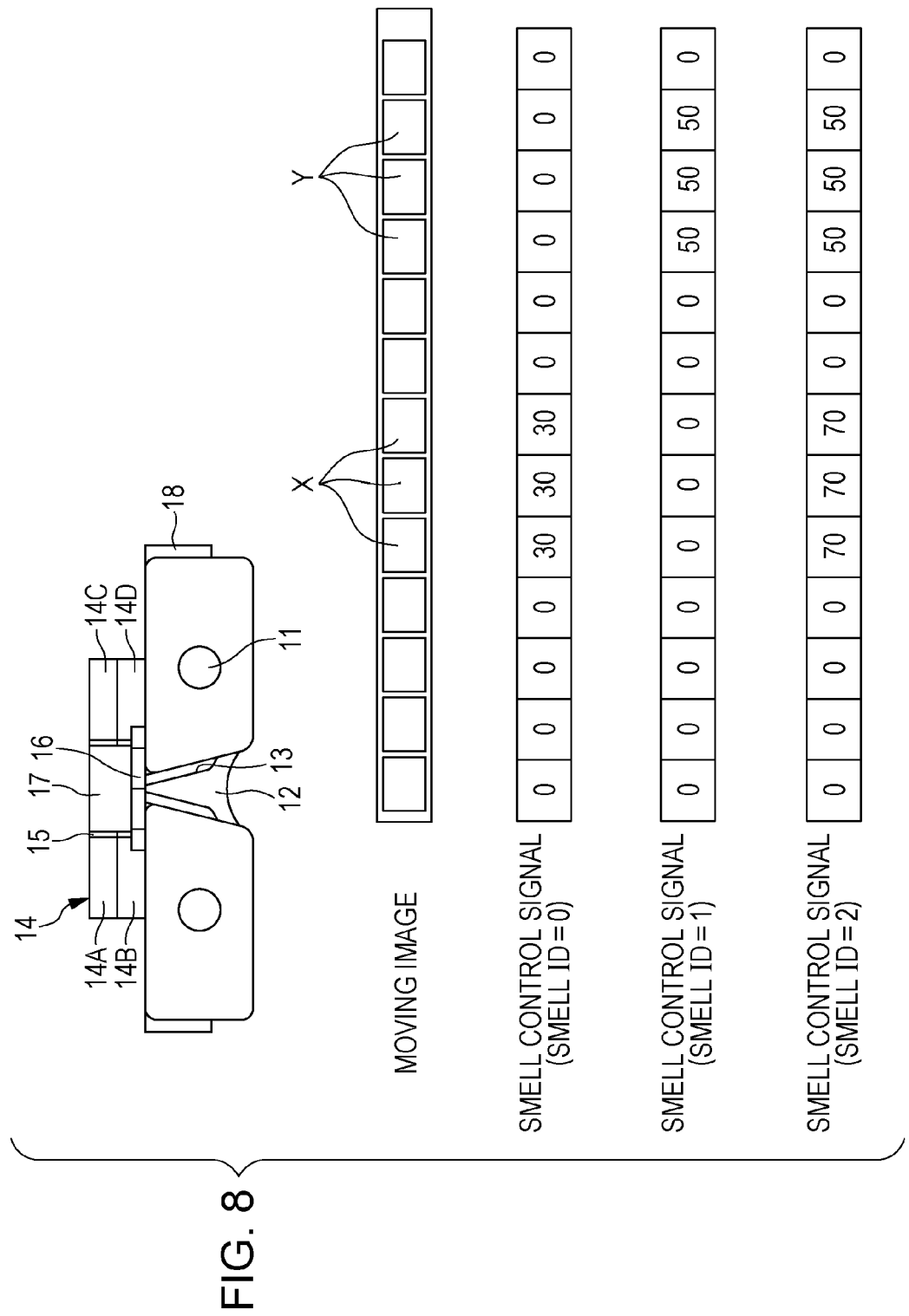

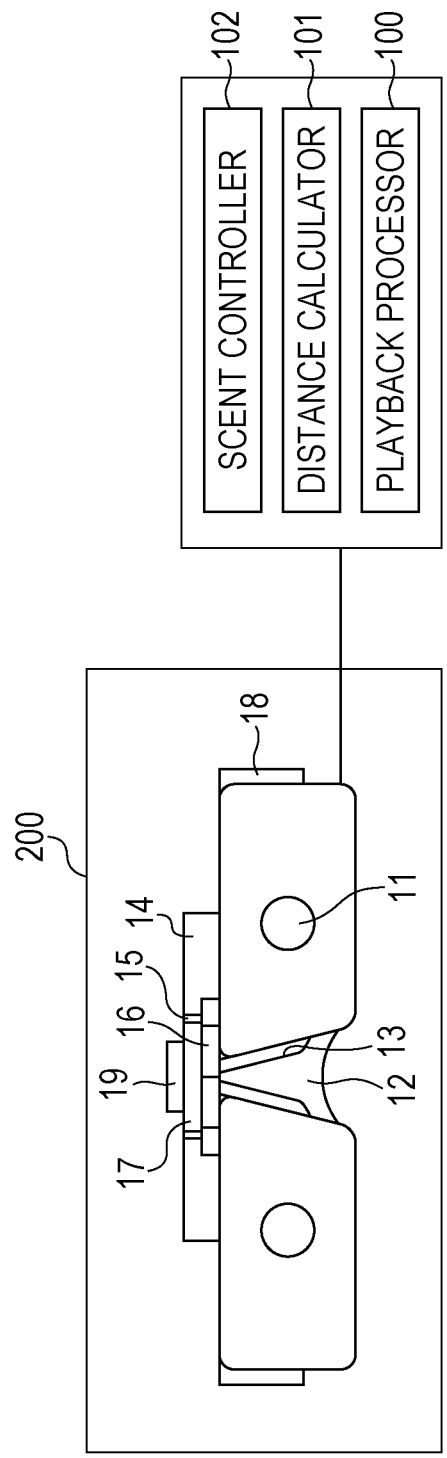

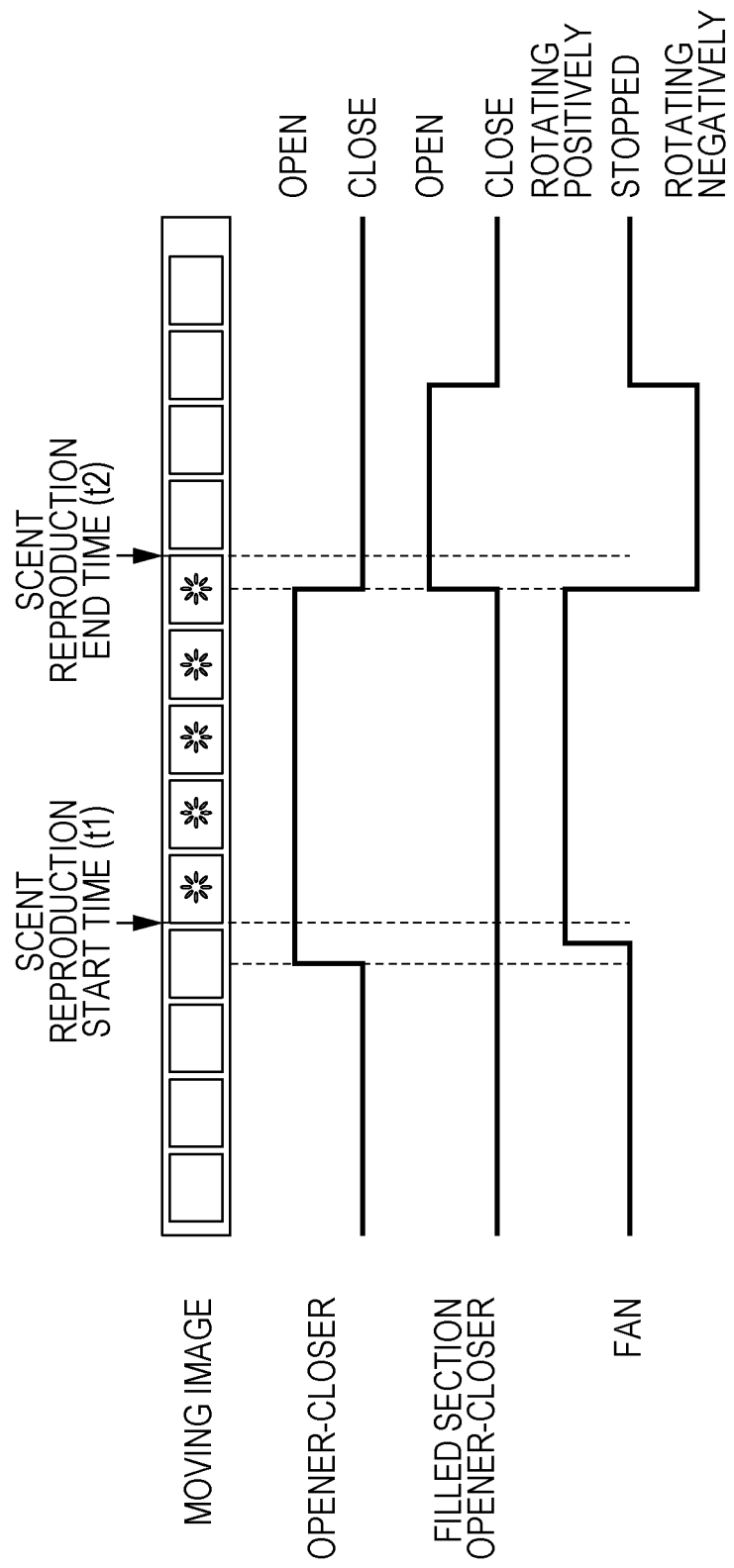

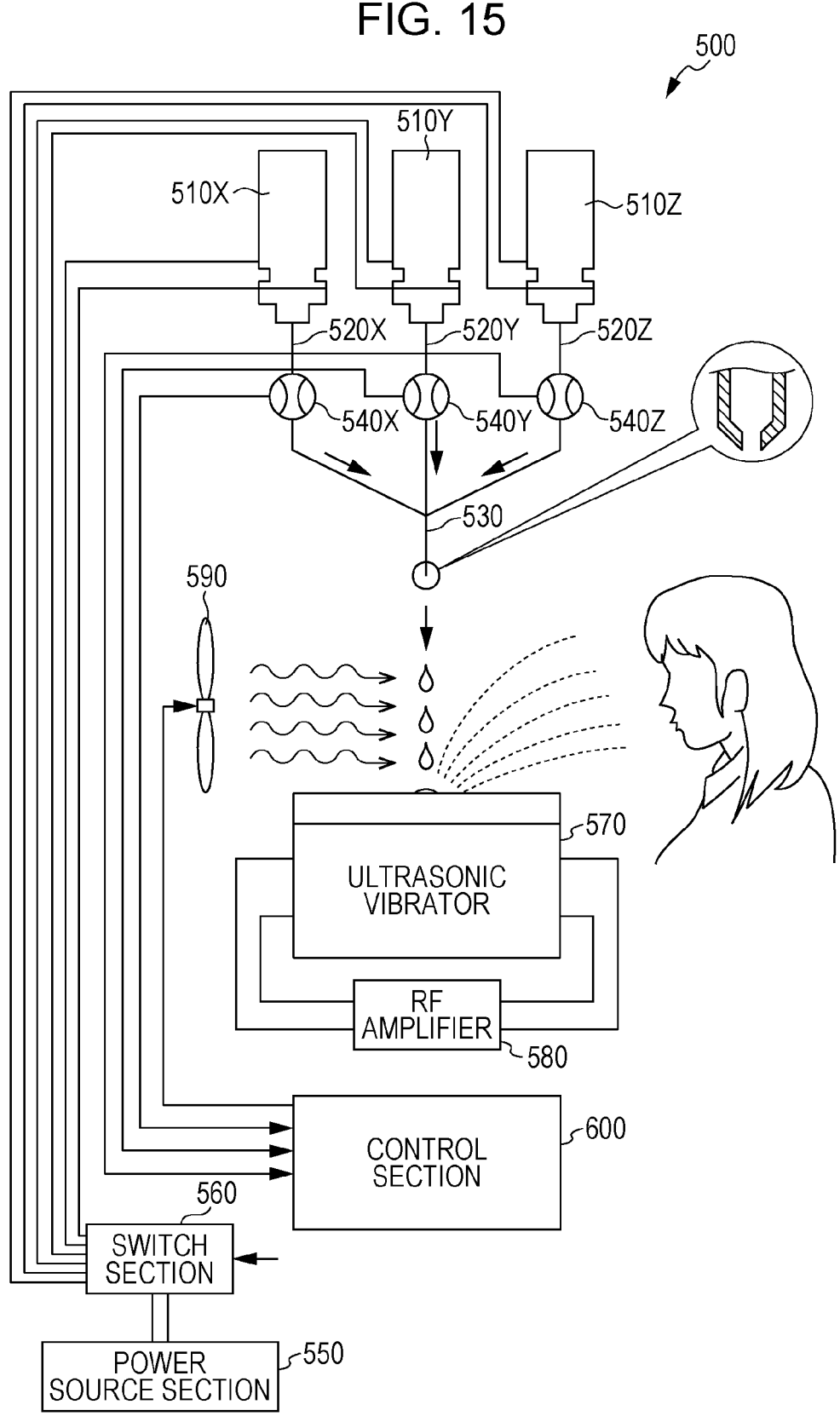

HEAD-MOUNTED PERFUME DISPENSER APPARATUS

BACKGROUND

1. Technical Field

The present disclosure relates to a smell reproduction apparatus.

2. Description of the Related Art

Attempts have been started to present olfactory information to a user in recent years (see, for example, Japanese Unexamined Patent Application Publications Nos. 2011-184486 and 2013-74476).

SUMMARY

Japanese Unexamined Patent Application Publications Nos. 2011-184486 and 2013-74476 described above need further improvement.

In one general aspect, the techniques disclosed here feature a head-mounted display including a playback processor which plays back a moving image from first time until second time, the first time corresponding to timing of starting playback of the moving image and the second time corresponding to timing of ending playback of the moving image, a box for placing a container containing a perfume inside, a filled section which is temporarily filled with the perfume and emits the temporarily filled perfume according to starting playback of the moving image, and a tubular vent hole which is in contact with a nose of a user when the user wears the head-mounted display.

An aspect of the present disclosure achieves the further improvement.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 6 is a diagram for explaining a smell box set value;

FIG. 8 is a diagram for explaining a method for mixing a plurality of smells;

FIG. 9 is a diagram of a configuration of a smell reproduction apparatus according to a second embodiment of the present disclosure;

FIG. 12 is a timing diagram of the operations of an opener-closer, a sending section, and a filled section opener-closer according to the third embodiment of the present disclosure;

FIG. 15 is a diagram of a configuration of a conventional smell reproduction apparatus.

Figure 1:
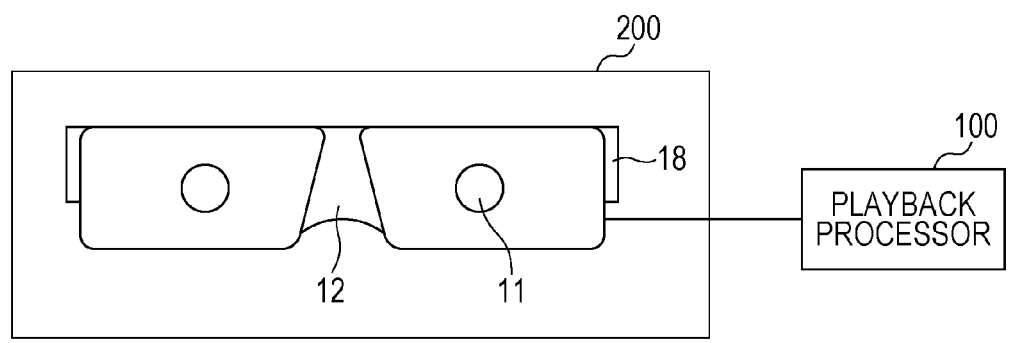
FIG. 1 is a diagram of an overall configuration according to a first embodiment of the present disclosure.

DETAILED DESCRIPTION (Underlying Knowledge Forming Basis of the Present Disclosure)

The present inventor has found that the techniques disclosed in Japanese Unexamined Patent Application Publications Nos. 2011-184486 and 2013-74476 cause the problems below.

FIG. 15 shows a smell generation apparatus disclosed in Japanese Unexamined Patent Application Publication No. 2011-184486.

In FIG. 15, a smell generation apparatus 500 includes a plurality of electroosmotic flow pumps 510X, 510Y, and 5102, a plurality of pipes 520X, 520Y, and 520Z, a merging pipe 530, a plurality of liquid quantity sensors 540X, 540Y, and 540Z, a power source section 550, a switch section 560, an ultrasonic vibrator 570, a radio frequency (RF) amplifier 580, a blowing section 590, and a control section 600.

Figure 16:
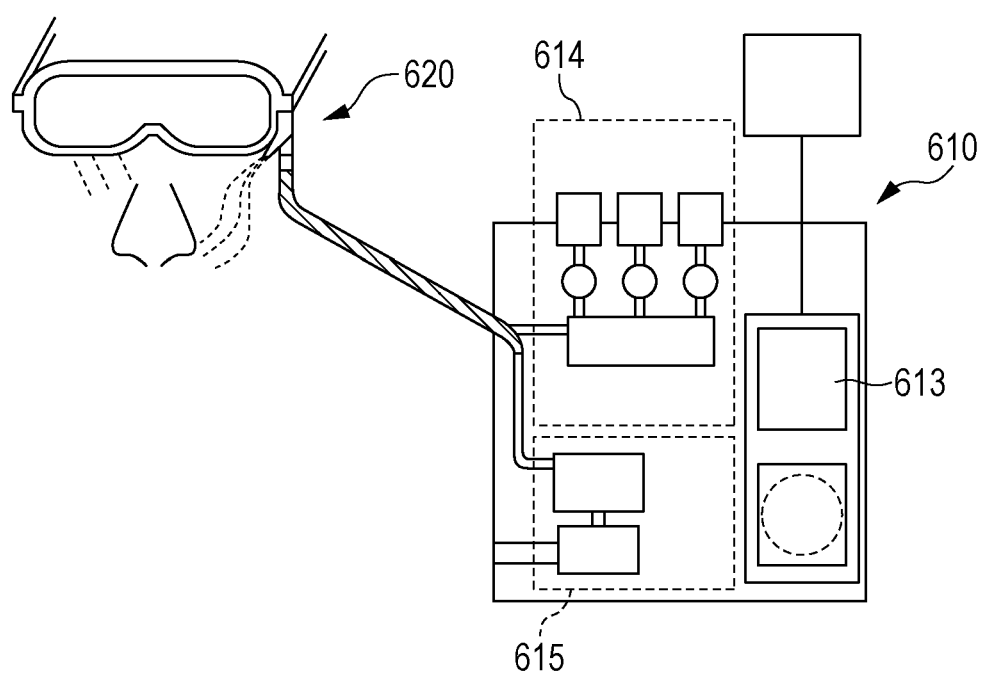
FIG. 16 is a diagram of a configuration of a conventional scent reproduction system.

FIG. 16 shows a scent provision system disclosed in Japanese Unexamined Patent Application Publication No. 2013-74476.

In FIG. 16, a reproduction system 610 which plays back a moving image medium with sound and a scent provision apparatus 620 which emits a scent provided by the reproduction system 610 are provided. The reproduction system 610 is provided with a scent information processing section 613 which generates a control signal for scent generation, a scent generation section 614 which generates a desired scent on the basis of a control signal output from the scent information processing section 613, and a cleaning section 615 which gets rid of a scent collected from the air. The scent provision apparatus 620 is mounted on an eyeglass type display which a user wears and receives a scent together with a picture.

However, the apparatus disclosed in Japanese Unexamined Patent Application Publication No. 2011-184486 and the system disclosed in Japanese Unexamined Patent Application Publication No. 2013-74476 suffer from the problem of user-unfriendliness due to large configuration.

Under the circumstances, the present inventor has studied the remedial measures below.

(1) A head-mounted display according to an aspect of the present disclosure is a head-mounted display including a playback processor which plays back a moving image from first time until second time, the first time corresponding to timing of starting playback of the moving image and the second time corresponding to timing of ending playback of the moving image, a box for placing a container containing a perfume inside, a filled section which is temporarily filled with the perfume and emits the temporarily filled perfume according to starting playback of the moving image, and a tubular vent hole which is in contact with a nose of a user when the user wears the head-mounted display.

(2) In the aspect, the filled section may have a first opener-closer at an upper portion, in which the first opener-closer may open according to ending playback of the moving image.

(3) In the aspect, the smell reproduction system may further include a fan above the vent hole and below the filled section.

(4) In the aspect, the smell reproduction system may further include a gyro which senses a direction that the user faces.

(5) In the aspect, the vent hole may include one left vent hole and one right vent hole.

(6) In the aspect, the fan may include one left fan and one right fan.

(7) In the aspect, the smell reproduction system may further include a second opener-closer between the box and the filled section, and the second opener-closer may open and close according to starting and ending playback of the moving image.

(8) In the aspect, starting of rotation, the fan rotates both forward and backward, opening and closing of the first opener-closer, opening and closing of the second opener, stopping and stopping of rotation of the fan, rotation direction of the fan and the number of revolutions of the fan may be controlled in accordance with a control signal.

(9) In the aspect, the control signal may be a sound signal which is included in the moving image.

(10) In the aspect, the control signal may be a MIDI signal corresponding to the moving image.

(11) In the aspect, the smell reproduction system may further include a control signal processor which generates the control signal.

(12) In the aspect, the second opener-closer may open at third time and closes at fourth time, the third time being before the first time according to the control signal, and the fourth time being after the first time and before the second time, the first opener-closer may open at the fourth time and closes at fifth time according to the control signal, the fifth time being after the second time, the fan may rotate forward at the third time or sixth time according to the control signal, the sixth time being after the third time and before the first time, and the fan may rotate backward at the fourth time according to the control signal, the fan may stop at the fifth time according to the control signal.

(13) In the aspect, the smell reproduction system may further include a distance calculator which calculates a distance between an object in the moving image and the nose of the user on a basis of the sensed direction and a predetermined position of the object in the moving image, the object being a source of a smell corresponding to the emitted perfume, and a scent controller which performs control to change the number of revolutions of the fan in accordance with the calculated distance.

Embodiments of the present disclosure will be described below with reference to the drawings.

FIG. 1 shows a configuration of a smell reproduction system. The smell reproduction system is composed of a playback processor 100 which plays back a roving image and a smell reproduction apparatus 200 which provides a smell. As shown in FIG. 1, the playback processor 100 is integral with the smell reproduction apparatus 200.

The smell reproduction apparatus 200 is a head-mounted display and odes lenses 11 for enlarging a displayed picture and guiding the picture to eyes, a central section 12, and temple sections 18.

A user views an image through the lenses 11. The central section 12 is a recessed portion for causing the head-mounted display to engage with a nose of the user. The temple sections 18 are portions to be hooked over ears of the head-mounted display. The playback processor 100 provides a moving image to be played back to the smell reproduction apparatus 200. A moving image may be played back by playing back a medium, such as a DVD or a BD, or by downloading or streaming a moving image file on a network. An object to be played back is not limited to a moving image, and a game image may be provided.

A smell playback processor according to the present disclosure will be described below in a first embodiment.

First Embodiment

Figure 2:
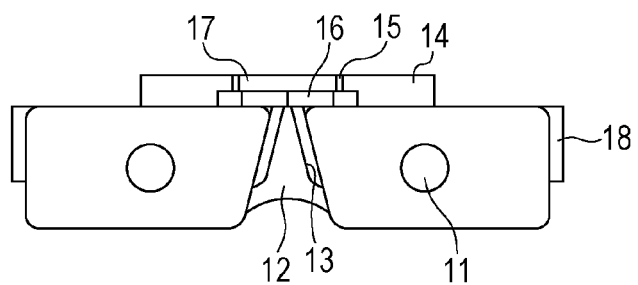
FIG. 2 is a diagram of a configuration of a smell reproduction apparatus according to the first embodiment of the present disclosure.

FIG. 2 shows a configuration of a smell reproduction apparatus 200 according to the present disclosure.

The smell reproduction apparatus 200 is of head-mounted display type. The smell reproduction apparatus 200 is particularly marked by constituent features (vent holes 13, smell boxes 14, opener-closers 15, and a fan 16) for reproducing a smell besides an image display section like a liquid crystal panel.

Note that the configuration except for features of the present disclosure will not be described in detail but a configuration of a conventional head-mounted display can be used. A head-mounted display according to the present disclosure is not limited to a smell reproduction apparatus with the configuration shown in FIG. 2.

Each vent hole 13 is tubular, and an opening is located near an upper portion of a nose when a user wears the smell reproduction apparatus 200.

A container containing a perfume can be placed in each smell box 14. A smell can be changed by changing a container.

Each opener-closer 15 is closed under normal conditions and is opened to release a smell in the corresponding smell box 14.

The fan 16 rotates so as to emit the smell remaining in the filled section 17 through the vent holes 13. Two fans 16 are desirably mounted such that left and right ones can be controlled independently of each other, but even one will do.

The filled section 17 is filled with part of a smell from the smell boxes 14.

The operation of the smell reproduction apparatus with the above-described configuration will be described with reference to FIGS. 2 and 3.

Figure 3:
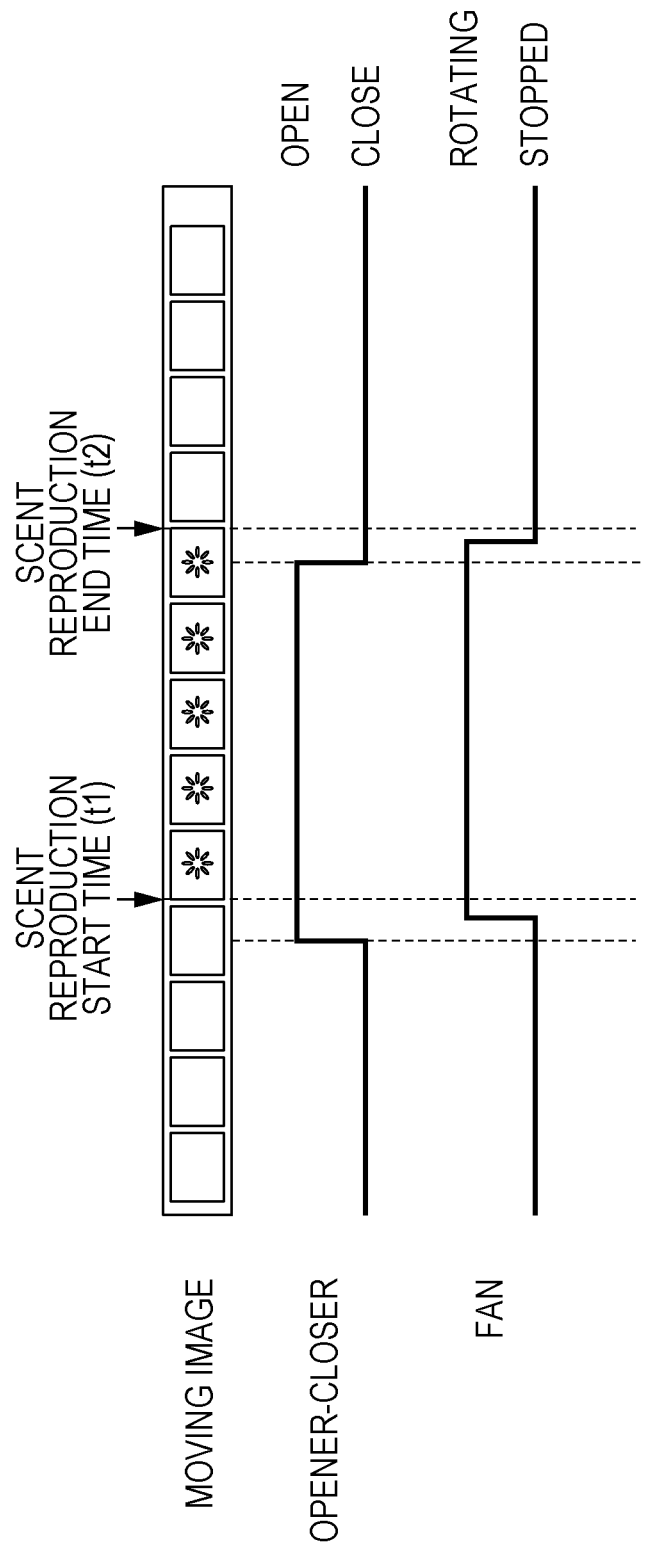
FIG. 3 is a timing diagram of the operations of are opener-closer and a fan according to the first embodiment of the present disclosure.

FIG. 3 is a timing diagram of the operations of the opener-closers 15 and the fan 16 according to the first embodiment.

A container containing a perfume corresponding to a moving image to be played back is placed in each smell box 14.

When playback of the moving image is started, the opener-closers 15 are opened several seconds before timing of smell emission (a scent reproduction start time t1). At the same time as or slightly later than the opening, the fan 16 starts rotating.

The rotation of the fan 16 creates an airflow. The smell of the perfume travels from the smell boxes 14 to a nose through the filled section 17 and the vent holes 13.

Finally, the opener-closers 15 are closed before a scent reproduction end time (t2), and rotation of the fan 16 is then stopped.

The earlier closing of the opener-closers 15 stops a smell from entering the filled section 17. A smell remaining in the filled section 17 is discharged by the fan 16 after the closing, which stops a smell from floating out continuously.

The stopping of rotation of the fan 16 stops air from flowing, and the nose no longer senses a smell.

For example, a sound signal may be used to control rotation of the fan 16. Use of a low-frequency sinusoidal signal as a single-channel sound signal of a multichannel sound signal accompanying a moving image file to control the fan 16 removes the need for a particularly complicated control section.

A sound signal belonging to another channel may be similarly used to control the opener-closers 15. Alternatively, a control signal shared with the fan 16 may be used.

For example, a common control sound signal for the opener-closers 15 and the fan 16 is used in the manner below. A sound signal may be reproduced in advance to control the opener-closers 15, and the sound signal for controlling the opener-chasers 15 may be subjected to delay processing and used as a control sound signal for the fan 16.

As another example of a control signal, a MIDI signal may be used. If a MIDI signal is used, a scent controller may be provided in the playback processor 100 or the smell reproduction apparatus 200 to control the fan 16 and the opener-closers 15 in accordance with a MIDI signal.

Note that smell control metadata indicating whether to enable or disable smell emission may be prepared to control rotation of the fan 16. Each control metadata entry indicates the absence of a smell when the entry has a value of 0 and the presence of a smell when the entry has a value of 1.

A control metadata entry is set in each video frame of a video stream. This allows judgment as to whether to emit a smell in one in question of the video frames.

Figure 4:
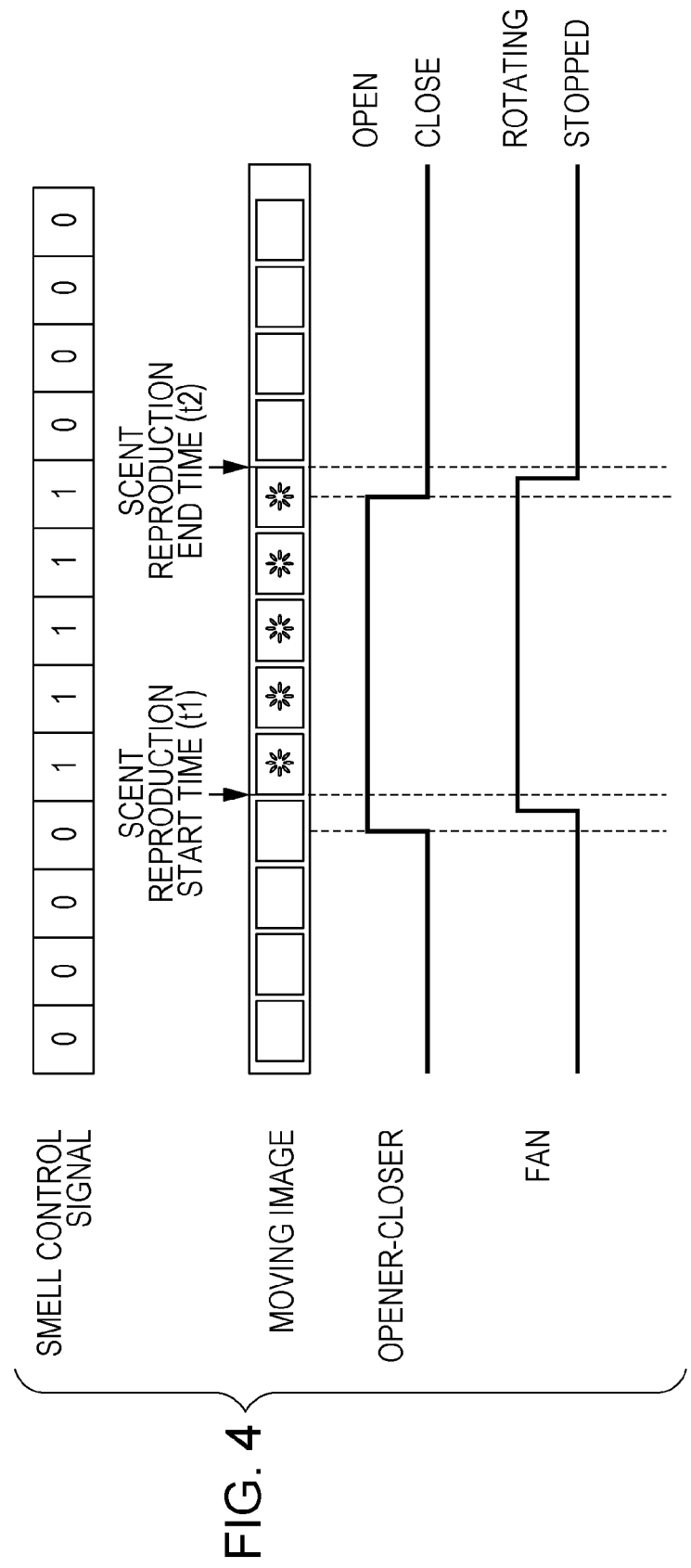
FIG. 4 is a timing diagram with a signal added thereto which is defined by smell control metadata.

FIG. 4 shows the timing diagram in FIG. 3 with a smell control signal added thereto which is obtained by reproducing metadata. As shown in FIG. 4, the scent reproduction start time (t1) and the scent reproduction end time (t2) are defined by a period when the smell control signal is 1.

A piece of control metadata may be stored in, for example, an area (for example, user data in the case of MPEG-2 or an SEI message in the case of MPEG-4 AVC) storing supplemental data of each video frame of a video stream. With this configuration, rotation control of the fan based on smell control metadata at timing of decoding and displaying a video stream removes the need for a complicated control section and allows control of smell emission synchronized with a picture. Note that a piece of smell control metadata need not be stored in every video frame and may be stored in a top frame of a GOP.

The above-described control signals (a sound channel, a MIDI signal, and control metadata) used to control smell emission will be simply referred to as a smell control signal hereinafter.

Application of First Embodiment

Figure 5A:
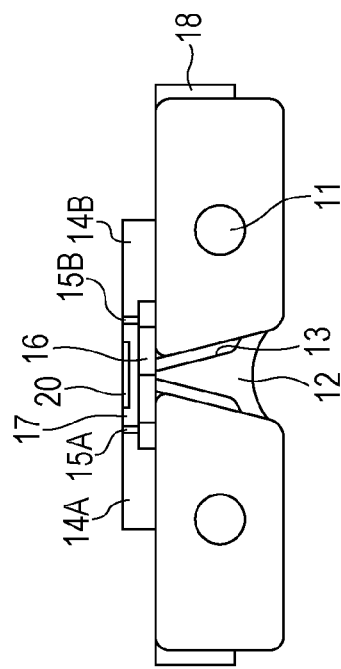
FIGS. 5A and 5B are diagrams for explaining a configuration to store different smells.
Figure 5B:
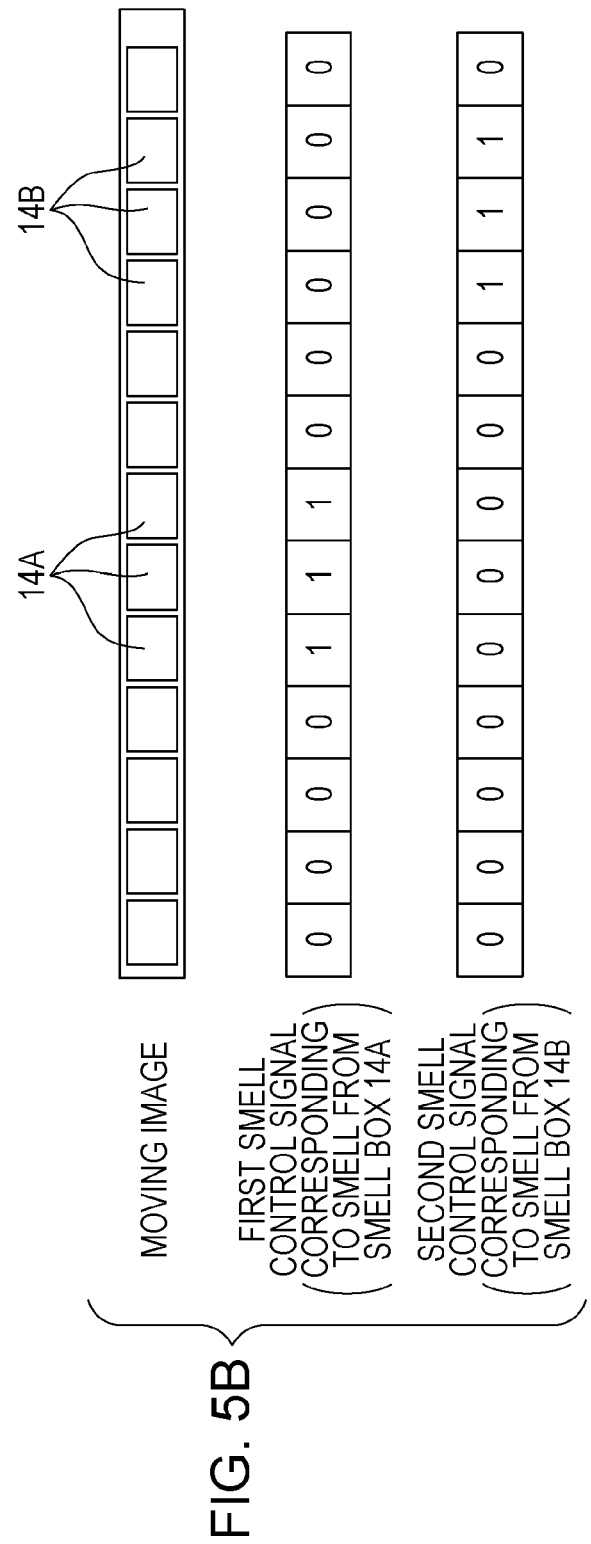

FIGS. 5A and 5B show a configuration of a smell reproduction apparatus when different smells are stored.

To implement sending of a plurality of different smells, perfumes serving as sources of different smells are stored in a smell box 14A and a smell box 14B, as shown in FIG. 5A. Opener-closers 15A and 15B open and close respective doors to the smell boxes 14A and 14B.

Pieces of timing information for emitting the perfumes are separately stored in a moving image. For example, FIG. 5B shows an example of the configuration of control metadata. Two pieces of control data, a first smell control signal specifying scent reproduction timing for the smell box 14A and a second smell control signal specifying scent reproduction timing for the smell box 14B, are prepared. The smell reproduction apparatus judges the smell emission timing for the smell boxes 14A and 14B by referring to the pieces of information.

The smell reproduction apparatus opens only the opener-closer 15A if the smell reproduction apparatus judges, by referring to the first smell control signal, that it is time to send a scent from the smell box 14A and opens only the opener-closer 15B if the smell reproduction apparatus judges, by referring to the second smell control signal, that it is time to send a scent from the smell box 14B.

With the above-described configuration, a plurality of different smells can be provided to a user during same content. Note that lack of direct connection between the smell boxes 14A and 14B and the vent holes 13 and the presence of the filled section 17 that is temporarily filled avow implementation of provision of a plurality of different smells. If the opener-closers 15A and 15B are controlled by the process of storing a low-frequency sinusoidal signal as a single-channel sound signal of a multichannel sound signal accompanying a moving image file, as described above, respective channels may be prepared for the plurality of smells. The same applies to a case using a MIDI signal, and a plurality of MIDI signals may be stored.

(Sending of Smell Suited to Loading Status)

In the first embodiment, smell emission is controlled in accordance with a control signal set in a moving image. The configuration may be such that a smell emission method can be selected in accordance with a users preferences or the loading status of the smell boxes 14. A specific configuration will be described.

FIG. 6 is a diagram for explaining a smell box set value. As shown on the right side of FIG. 6, a smell reproduction system includes a smell box set value, a scent controller, and a playback processor.

A piece of smell control information stored in a moving image has a smell ID which is set for a corresponding smell. The smell reproduction system has the added "smell box set value" indicating whether to send a smell specified in the moving image.

For example, a plurality of smells are prepared for a moving image, and pieces of control data having a smell ID of 0 and a smell ID of 1 are stored in the moving image. In this case, if only a perfume with the smell ID of 1 is stored in loaded smell boxes 14A and 14B, the smell box set value has only the smell ID of 1. A smell reproduction apparatus refers to the smell box set value, refers to only a control signal with the specified smell ID, and emits a smell.

Note that the smell box set value may be set by a user through a GUI or the like even when necessary smell boxes are loaded. With this configuration, a smell suited to a users preferences or a situation can be emitted during a moving image, for which a plurality of perfumes serving sources of smells are set.

The smell box set value may be automatically set at the time of smell box loading. For example, a configuration is conceivable in which an NFC chip storing information, such as a smell ID of a corresponding scent, is embedded in each smell box, and the smell reproduction apparatus has an NFC communication function. The smell reproduction apparatus can judge which perfume the loaded smell box stores by reading the information of the NFC chip in each smell box through NFC communication. All smell boxes preferably have unique smell IDs.

(Quantification of Smell)

A piece of information obtained by quantifying a smell may be included in a piece of information to be stored as the smell box set value or a smell control signal to be stored in a moving image. An example of smell quantification is a method adopted in a smell identification device by SHI-MADZU CORPORATION. There are various methods for smell quantification.

The smell reproduction apparatus may select a smell box to be opened and closed in accordance with the degree of closeness to a piece of quantified information stored as the smell box set value (the degree of closeness is higher if an absolute value of a difference is smaller).

For example, if a smell value of a smell control signal with the smell ID of 0 included En a moving image is 100, a smell value of a smell control signal with the smell ID of 1 included in the moving image is 200, and a smell value stored as the smell box set value is 180, smell control is performed using the smell control signal with the smell ID of 1, which has a smaller absolute value for a difference in value. With this configuration, a scent which is not the same as but close to a scent included in a moving image can be provided to a user. The user can make effective use of a smell box.

Note that, in this case, a threshold may be set for the degree of closeness. For example, assume that a smell value of a smell control signal with the smell ID of 0 included in a moving image is 100, a smell value of a smell control signal with the smell ID of 1 included in the moving image is 200, a smell value stored as the smell box set value is 1,000, and a smell threshold is 500. In this case, absolute values of differences for both smells exceed the threshold value of 500. The smell reproduction apparatus may judge that the smells are quite different to disable both the smells. With this configuration, a scent different from an impression of a user is not provided to the user any longer.

Note that a smell control signal may not be stored in a moving image and may be separately transmitted through a network. With this configuration, it is possible to easily change only a smell sent from an object by not changing video content, such as a moving image, but changing only a smell control signal.

(Expansion of Boxes)

Figure 7:
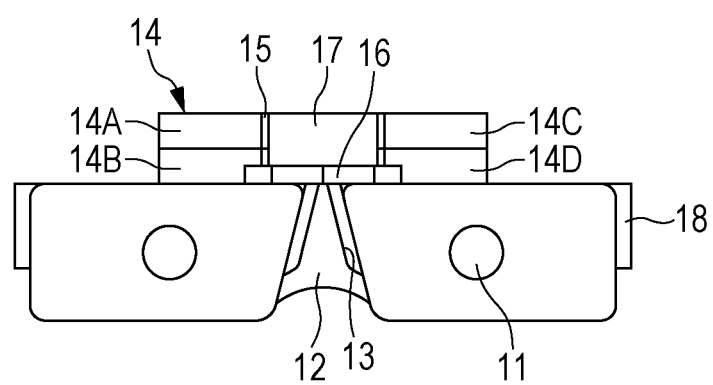
FIG. 7 is a diagram showing an example of a configuration to store two or more smell boxes.

Note that the number of boxes is not limited to two and can, of course, be expanded in the manner shown in FIG. 7. FIG. 7 shows an example of a configuration in which a smell reproduction apparatus stores three or more smell boxes.

For example, assume that four types of scents are stored, as in FIG. 7, and that sending of a scent from a smell box 14A is set in a smell control signal at the time of playback of a first picture. If only a smell control signal, in which whether to send a smell from a smell box 14B is set, is updated via a network at the time of playback of a next picture, a smell to be sent can be easily changed even during same content.

This can be applied in the manner below. For example, if a scent of a perfume used by an idol is updated in the form of a "smell control signal" every day in video content associated with the idol, a user can enjoy the idol video content every day together with a perfume used by the idol on the day.

(Addition of Mixture Proportion)

Note that smell control signals may include pieces of information indicating mixture proportions for smell boxes with different smells.

FIG. 8 is a diagram for explaining a method for mixing a plurality of smells. For example, in smell control signals for a moving image in FIG. 8, instructions for smell sending are given for a group of frames denoted by X and a group of frames denoted by Y. A value of each of control signals is a piece of information indicating a mixture proportion and is a percentage. That is, FIG. 8 shows that a smell sent in the group X of frames is a smell obtained by mixing a smell with a smell ID of 0 and a smell with a smell ID of 2 in proportions of 30% and 70%, respectively. Similarly, FIG. 8 shows that a smell sent in the group Y of frames is a smell obtained by mixing a smell with a smell ID of 1 and the smell with the smell ID of 2 in proportions of 50% and 50%, respectively. To mix smells in such mixture proportions, a smell reproduction apparatus may adjust the number of revolutions of the fan 16.

With this configuration, various smells can be created even with a small number of smell boxes. Calculation of a smell mixture proportion parameter may be implemented in a cloud system, and only a result of the calculation may be transmitted as a smell control signal over a network. This allows updating of content without complicated processing on the reproduction apparatus side.

Second Embodiment

FIG. 9 is a diagram of a configuration of a smell reproduction apparatus according to a second embodiment of the present disclosure. In FIG. 9, same components as those in the smell reproduction apparatus in FIGS. 1 and 2 are denoted by same reference numerals, and a description thereof will be omitted.

The smell reproduction apparatus in FIG. 9 is different from the smell reproduction apparatus in FIG. 2 in that a gyro 19 is provided. FIG. 9 is different from FIG. 2 in that a distance calculator 101 and a scent controller 102 are provided in addition to a playback processor 100. The operation of the smell reproduction apparatus with the above-described configuration will be described with reference to FIGS. 10A and 10B together with FIG. 9.

Figure 10A:
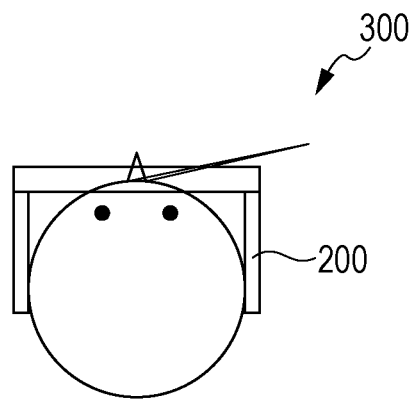
FIG. 10A is a diagram showing a positional relationship between an object and an operator according to the second embodiment of the present disclosure.
Figure 10B:
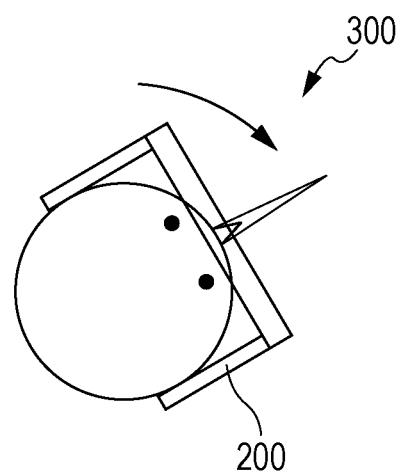
FIG. 10B is a diagram showing a positional relationship between the object and the operator according to the second embodiment of the present disclosure.

FIGS. 10A and 10B are diagrams showing positional relationships between an object and an operator according to the second embodiment of the present disclosure. A position serving as a source of a smell is set in advance in a moving image to be played back. For example, assume that an object 300 which reproduces a smell is located to the right of a person wearing the smell reproduction apparatus, as shown in FIG. 10A. The person wearing the smell reproduction apparatus faces to the right and looks toward the object 300, as in FIG. 10B. At this time, which direction the person faces is detected by the gyro 19 attached to the smell reproduction apparatus. A distance between the person wearing the smell reproduction apparatus and the object 300 is calculated by the distance calculator 101. As the distance becomes shorter, the scent controller 102 increases the number of revolutions of a fan 16, and the person wearing the smell reproduction apparatus comes to smell the object 300. The distance calculator 101 may calculate distances to left and right halves of a nose independently of each other to thereby control the numbers of revolutions of the left and right fans 16 independently of each other or make a distinction between left and right rotation time periods.

Third Embodiment

Figure 11:
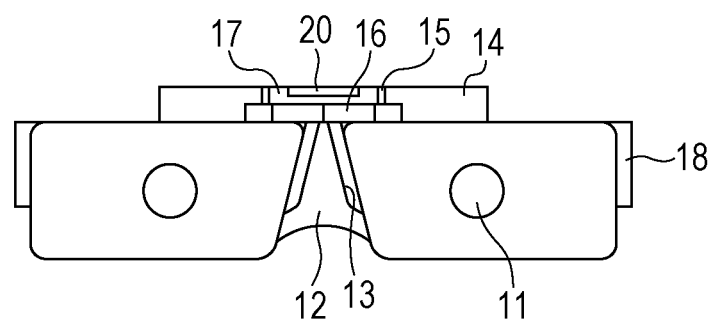
FIG. 11 is a diagram of a configuration of a smell reproduction apparatus according to a third embodiment of the present disclosure.

FIG. 11 is a diagram of a configuration of a smell reproduction apparatus according to a third embodiment of the present disclosure. In FIG. 11, same components as those in the smell reproduction apparatus in FIG. 2 are denoted by same reference numerals, and a description thereof will be omitted.

In FIG. 11, the smell reproduction apparatus is different from the smell reproduction apparatus in FIG. 2 in that a filled section 17 has a filled section opener-closer 20. The operation of the smell reproduction apparatus with the above-described configuration will be described with reference to FIG. 12 together with FIG. 11.

FIG. 12 is a timing diagram of the operations of an opener-closer 15, a fan 16, and the filled section opener-closer 20 according to the third embodiment of the present disclosure.

A container containing a perfume which is fitted to, for example, a moving image to be played back is first placed in each smell box 14.

When playback of the moving image is started, the opener-closers 15 are opened several seconds before timing of smell emission (a scent reproduction start time t1). At the same time as or slightly later than the opening, the fan 16 starts being positively rotated. The positive rotation causes air to flow toward vent holes 13. The positive rotation of the fan 16 creates an airflow. A smell travels from the smell boxes 14 to a nose through the filled section 17 and the vent holes 13.

The opener-closers 15 are then closed before a scent reproduction end time (t2). At the same time, the filled section opener-closer 20 is opened.

Finally, the fan 16 is negatively rotated.

The earlier closing of the opener-closers 15, the opening of the filled section opener-closer 20, and the negative rotation of the fan 16 cause air to flow against the vent holes 13. That is, a smell remaining in the filled section 17 is discharged through the filled section opener-closer 20. After the negative rotation of the fan 16, the filled section opener-closer 20 is closed, and rotation of the fan 16 is stopped. In this manner, the smell remaining in the fired section 17 can be discharged.

The filled section opener-closer 20 is configured to be openable and closable with timing, as described above. An air hole may be formed in an upper portion of the filled section 17. Note that a smell enable/disable button may be provided at the smell reproduction apparatus and that the smell reproduction apparatus may refer to the status of the smell enable/disable button and perform smell emission control.

In this case, when smell emission is disabled, the smell reproduction apparatus closes the opener-closers 15 to prohibit smell emission even if smell sending is specified by a smell control signal. With this configuration, a user can easily make an adjustment to enable or disable smell emission in accordance with a situation or preferences. Such a button is preferably located in the vicinity of a central section 12 that is close to the position of a nose of the user because the user intuitively knows the position of the button. A gesture recognition function, such as Kinect, may be used, and a nose-pinching gesture may be used as an operation of enabling or disabling smell emission.

Note that the smell reproduction apparatus may be provided with a button or a slide switch for setting smell level and that the smell reproduction apparatus may refer to the smell level and perform smell emission control.

In this case, the smell reproduction apparatus adjusts the intensity of smell in accordance with the smell level. More specifically, the smell reproduction apparatus adjusts the number of revolutions of the fan 16. With this configuration, a user can easily adjust the intensity of smell in accordance with a situation or preferences. Such a button is preferably located in the vicinity of the central section 12 that is close to the position of the nose of the user because the user intuitively knows the position of the button.

Note that although a system which emits a smell synchronously with a picture has been described in the present embodiment, the present disclosure is not limited to smell emission synchronous with a picture. If the user can select between synchronism and asynchronism using a GUI menu or the like and can select a smell box to emit a smell in the case of asynchronism, smell emission asynchronous with a picture can be implemented.

Application of Third Embodiment

The present application is intended for interlock with a moving image recorded in real time.
(Sense of Augmented Reality Using Smell)

Figure 13A:
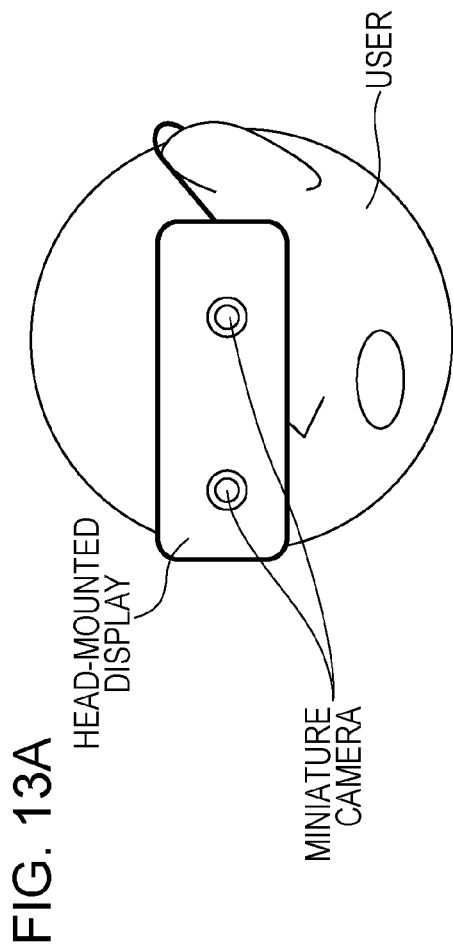
FIG. 13A is a diagram for explaining a configuration which provides a sense of augmented reality using a smell.
Figure 13B:
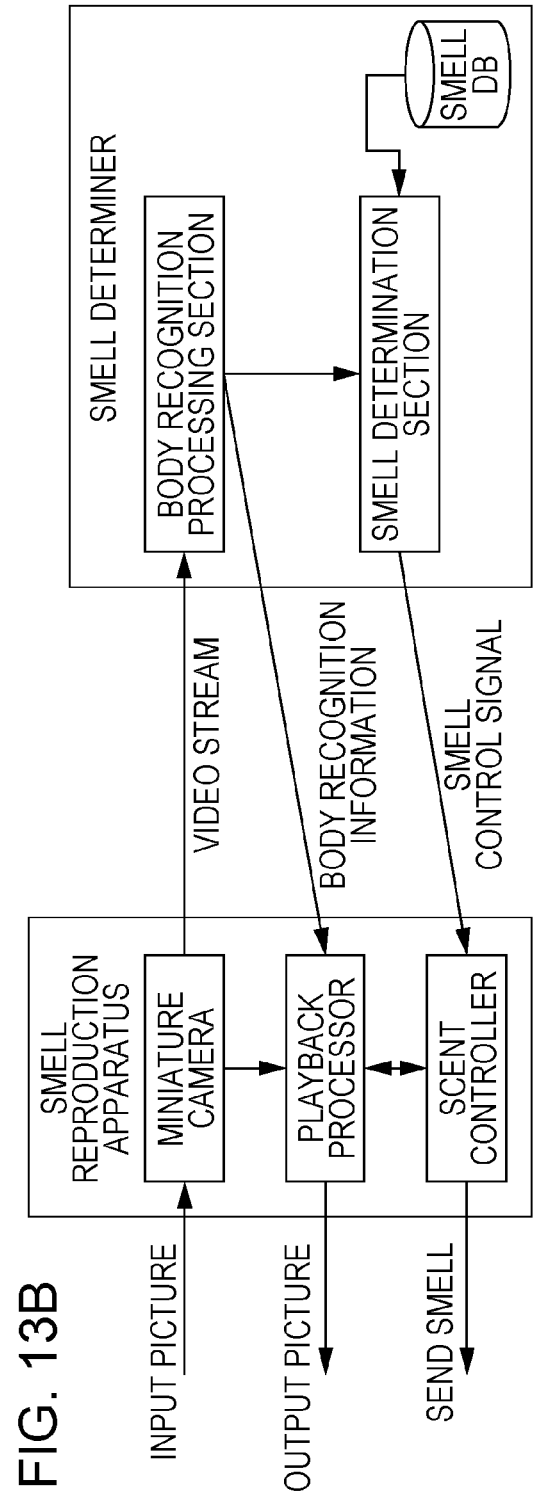
FIG. 13B is a diagram for explaining the configuration that provides a sense of augmented reality using a smell.

FIGS. 13A and 13B are diagrams for explaining a configuration which provides a sense of augmented reality using a smell. In particular, if cameras are mounted at eyeglass sections of a smell reproduction apparatus, as shown in FIG. 13A, moving images taken by the cameras are displayed without change, and a smell is changed depending on the content of the images, an augmented reality effect can be given.

A specific system configuration is shown in FIG. 13B. In FIG. 13B, the smell reproduction apparatus has the additional miniature cameras. The miniature cameras are set at the positions of eyes when a user wears the smell reproduction apparatus, and the user can receive pictures at the specified positions.

Pictures taken by the miniature cameras are transmitted to a playback processor and are compressed as video streams and transmitted to a smell determiner. The playback processor displays the pictures output from the miniature cameras on a display on the smell reproduction apparatus without change. A scent controller of the smell reproduction apparatus emits a smell on the basis of a smell control signal received from the smell determiner.

The smell determiner is composed of a body recognition processing section and a smell determination section.

The body recognition processing section decodes the input video streams, performs image recognition processing on a resultant picture, identifies a body in the picture, and inputs information on the body to the smell determination section.

The smell determination section refers to a smell DB and identifies a smell corresponding to the body. For example, the smell determination section selects a smell of a "banana" if there is a "banana" in the picture and a smell of a "freshscent perfume" if there is an idol in the picture. In this manner, the smell determination section identifies a piece of scent information corresponding to the body. The smell determination section creates a smell control signal and transmits the smell control signal to the smell reproduction apparatus.

With this configuration, an augmented reality effect corresponding to a picture actually viewed by a user can be achieved, and an emphasized smell can be delivered to the user. For example, amplification of a smell of food allows the user to enjoy a dish. An application is also conceivable which gives a weight loss effect to a user by sending a smell decreasing appetite.

The body recognition section may support an AR marker and be configured to determine an object to be displayed on an AR marker and transmit a result of the determination to the playback processor of the smell reproduction apparatus. The playback processor may create an object, such as 3DCG, and display the object superimposed on a picture displayed on the smell reproduction apparatus.

Figure 14A:
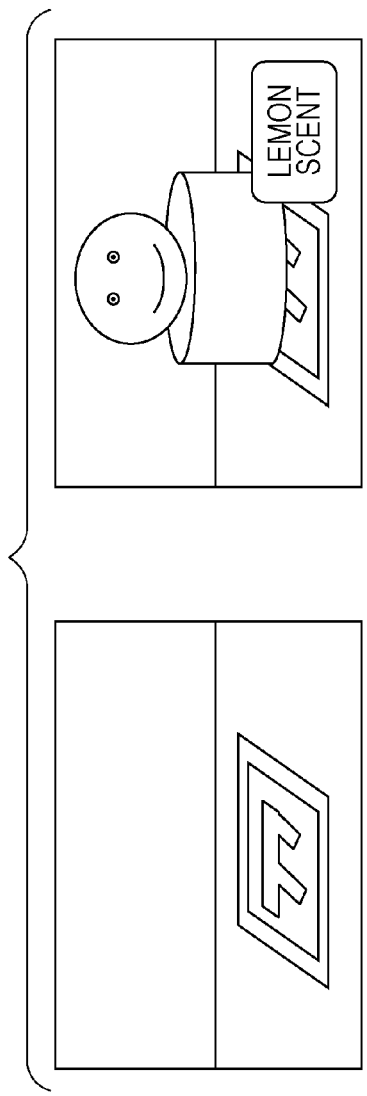
FIG. 14A is a timing diagram of the operations of the opener-closer, the sending section, and the filled section opener-closer according to the third embodiment of the present disclosure.

With this configuration, the smell reproduction apparatus can display an object corresponding to an AR marker to a user and send a smell corresponding to the object, as shown in FIG. 14A. A piece of scent information may be expressed as a piece of character information like "LEMON SCENT" in FIG. 14A, a color, or the like on a screen.

(Interlock with Perfume)

The sense of taste and a perfume have a close relationship. It is well known that a taste sensed by a human changes with a change in perfume. For example, if a human smells a chocolate while chewing tasteless gum, the human feels like chewing chocolaty gum.

For this reason, a smell different from the actual smell of a drink or a food is provided to a user, thereby making the user virtually experience feels of various foods.

Figure 14B:
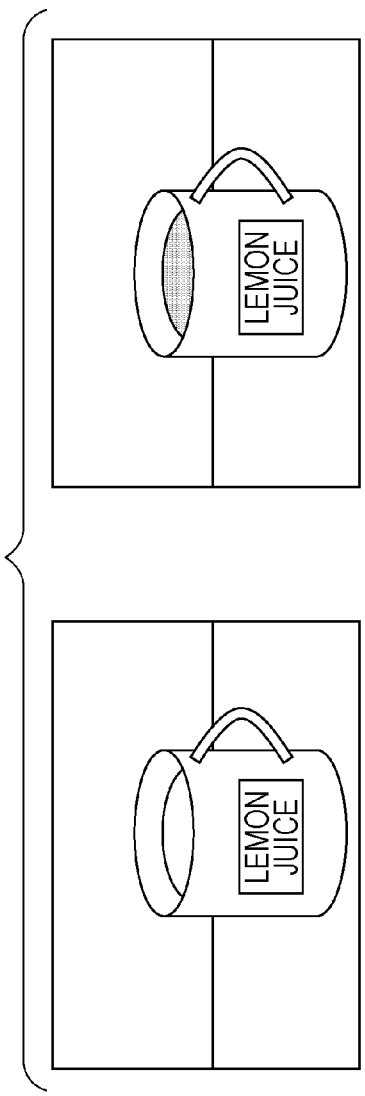
FIG. 14B is a timing diagram of the operations of the opener-closer, the sending section, and the filled section opener-closer according to the third embodiment of the present disclosure.

Referring to FIG. 14B, in a picture taken by the miniature cameras, a cup is labeled "LEMON JUICE". In fact, the cup contains not lemon juice but a sugar solution.

The smell determiner detects the label, judges that "LEMON JUICE" is denoted on the label, and transmits a smell control signal for lemon. The smell reproduction apparatus emits a lemon smell, and a user can enjoy a sense of drinking lemon juice in a simulated manner. If a liquid portion of the picture is simultaneously changed to lemon yellow, more effect can be obtained. Note that although the label "LEMON JUICE" is recognized to determine how a food or a drink is simulated, the smell reproduction apparatus may automatically make a determination on the basis of information of loaded smell boxes.

Note that a server on a network may play as sections which process calculations, such as a distance calculator and the smell determiner, in the present embodiment. This configuration allows device miniaturization.

A smell reproduction apparatus according to the present disclosure is a small-sized smell reproduction apparatus mounted on a head-mounted display. The smell reproduction apparatus is small-sized and can be easily used by a general user.

What is claimed is:

1. A head-mounted perfume dispenser apparatus comprising:
   a playback processor which plays back a moving image from a first time until a second time, the first time corresponding to a moving image playback start time and the second time corresponding to a moving image playback end time;
   a box, in which a container containing a perfume is received;
   a reservoir which is filled with the perfume received from the box and emits the perfume according to a start of the moving image playback;
   a tubular vent hole which is in contact with a nose of a user when the user wears the head-mounted perfume dispenser apparatus; and
   a first opener-closer provided between the box and the reservoir,
   wherein the first opener-closer opens and closes according to the start and an end of the moving image playback,
   the reservoir has a second opener-closer provided at an upper portion of the reservoir, and
   the second opener-closer opens according to the end of the moving image playback.

2. The head-mounted perfume dispenser apparatus according to claim 1, further comprising:
   a fan provided above the vent hole and below the reservoir.

3. The head-mounted perfume dispenser apparatus according to claim 2, further comprising:
   a gyro which senses a direction that the user faces.

4. The head-mounted perfume dispenser apparatus according to claim 1, wherein
   the vent hole includes one left vent hole and one right vent hole.

5. The head-mounted perfume dispenser apparatus according to claim 2, wherein
   the fan includes one left fan and one right fan.

6. The head-mounted perfume dispenser apparatus according to claim 1, further comprising a fan provided above the vent hole and below the reservoir, wherein
   the fan rotates both forward and backward,
   opening and closing the first opener-closer, opening and closing the second opener, starting and stopping a fan rotation, a fan rotation direction and a number of revolutions of the fan are controlled in accordance with a control signal.

7. The head-mounted perfume dispenser apparatus according to claim 6, wherein
   the control signal is a sound signal which is included in the moving image.

8. The head-mounted perfume dispenser apparatus according to claim 6, wherein
   the control signal is a MIDI signal corresponding to the moving image.

9. The head-mounted perfume dispenser apparatus according to claim 6, further comprising:
   a control signal processor which generates the control signal.

10. The head-mounted perfume dispenser apparatus according to claim 6, wherein
    the first opener-closer opens at a third time and closes at a fourth time according to the control signal, the third time being before the first time and the fourth time being after the first time and before the second time,
    the second opener-closer opens at the fourth time and closes at a fifth time according to the control signal, the fifth time being after the second time,
    the fan rotates forward at the third time or a sixth time according to the control signal, the sixth time being after the third time and before the first time, and
    the fan rotates backward at the fourth time according to the control signal, the fan stops at the fifth time according to the control signal.

11. The head-mounted perfume dispenser apparatus according to claim 3, further comprising:
    a calculator which calculates a distance between an object in the moving image and the nose of the user on a basis of the sensed direction and a position of the object in the moving image, the object being a source of a smell corresponding to the emitted perfume; and a controller which changes a number of revolutions of the fan in accordance with the calculated distance.

\* \* \* \* \*